United States Patent [19]

Böhm et al.

[11] Patent Number: 5,808,073

[45] Date of Patent: Sep. 15, 1998

[54] PREPARATION AND PURIFICATION OF PERYLENE-3,4-DICARBIMIDES

[75] Inventors: Arno Böhm, Mannheim; Willi Helfer, Friedelsheim, both of Germany

[73] Assignee: BASF Aktiengesellschaft, Ludwigshafen, Germany

[21] Appl. No.: 860,925

[22] PCT Filed: Jan. 12, 1996

[86] PCT No.: PCT/EP96/00117

§ 371 Date: Jul. 21, 1997

§ 102(e) Date: Jul. 21, 1997

[87] PCT Pub. No.: WO96/22331

PCT Pub. Date: Jul. 25, 1996

[30] Foreign Application Priority Data

Jan. 20, 1995 [DE] Germany ............ 195 01 737.4

[51] Int. Cl.⁶ .......... C07D 221/18; C07D 401/04; C07D 407/04; C07D 409/04
[52] U.S. Cl. .......................... 546/39; 106/498
[58] Field of Search .................. 546/39; 106/498

[56] References Cited

U.S. PATENT DOCUMENTS

| | | | |
|---|---|---|---|
| 5,405,962 | 4/1995 | Muellen | 546/27 |
| 5,472,494 | 12/1995 | Hetzenegger et al. | 106/493 |
| 5,650,513 | 7/1997 | Langhals | 546/38 |

FOREIGN PATENT DOCUMENTS 0 596 292  10/1992  European Pat. Off. .
486 491  11/1929  Germany .

OTHER PUBLICATIONS

Chemical Abstracts 85:20928, abstract of Nagao, Shikizai Kyokaishi (1976), vol. 49(1), pp. 29–34.
Chemical Abstracts 123:85915, abstract of Quante, Angew. Chem., Int. Ed. Engl. (1995), 34(12), pp. 1323–1325.
Chemical Abstracts 123:202037, abstract of DE 4338784, May 18, 1995.
Chima 48 (1994)503–505, Langhals.
Chemical Society of Japoan 52, 1723–1726 (1979), Nagao.

*Primary Examiner*—John Kight
*Assistant Examiner*—D. Margaret M. Mach
*Attorney, Agent, or Firm*—Oblon, Spivak, McClelland, Maier & Neustadt, P.C.

[57] ABSTRACT

Preparation of perylene-3,4-dicarbimides by reaction of a perylene-3,4,9,10-tetracarboxylic acid or of the corresponding anhydrides with a primary amine by performing the reaction in the presence of a tertiary nitrogen base as solvent and of a transition metal or transition metal salt as catalyst, and purification of perylene-3,4-dicarbimides obtained by reaction of a perylene-3,4,9,10-tetracarboxylic acid or of the corresponding anhydrides with a primary amine by heating the crude products initially in N-methylpyrrolidone and then treating the resulting N-methylpyrrolidone adducts in the presence of an organic diluent with a base, and if desired subjecting the subsequently isolated products to an additional treatment with an aqueous acid, and also novel perylene-3,4-dicarbimides and their use as fluorescent dyes, pigments or pigment additive precursors.

10 Claims, No Drawings

PREPARATION AND PURIFICATION OF PERYLENE-3,4-DICARBIMIDES

This application is a 371 of PCT/EP96/00167, filed Jan. 12, 1996.

BACKGROUND OF THE INVENTION

1. Field of the Invention

The present invention relates to a novel process for preparing perylene-3,4-dicarbimides by reacting a perylene-3,4,9,10-tetracarboxylic acid, or the corresponding anhydrides, with a primary amine.

The invention also relates to a novel process for purifying perylene-3,4-dicarbimides obained by reaction of a perylene-3,4,9,10-tetracarboxylic acid or of the corresponding anhydrides with a primary amine.

The invention finally relates to novel perylene-3,4-dicarbimides of the general formula Ia

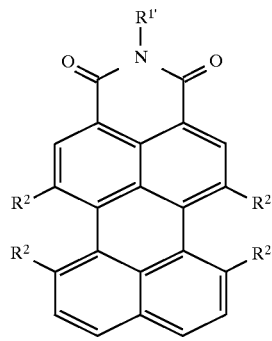

where
$R^{1'}$ is $C_{14}$–$C_{30}$-alkyl whose carbon chain may be interrupted by one or more of —O—, —S—, —$NR^3$—, —CO— and/or —$SO_2$— and which may be monosubstituted or polysubstituted by carboxyl, sulfo, hydroxyl, cyano, $C_1$–$C_6$-alkoxy or a 5-, 6- or 7-membered heterocyclic radical which is attached via a nitrogen atom and which may contain further heteroatoms and may be aromatic, where $R^3$ is hydrogen or $C_1$–$C_6$-alkyl;

$C_5$–$C_8$-cycloalkyl whose carbon skeleton may be interrupted by one or more of —O—, —S— and/or —$NR^3$—; phenyl which is monosubstituted or polysubstituted by $C_1$–$C_4$-alkyl or methoxy at least in the two ortho positions, by $C_5$–$C_{18}$-alkyl, $C_2$–$C_6$-alkoxy, halogen, hydroxyl, cyano, carboxyl, —$CONHR^4$, —$NHCOR^4$ and/or aryl- or hetarylazo, which may each be substituted by $C_1$–$C_{10}$-alkyl, $C_1$–$C_6$-alkoxy, halogen, hydroxyl, cyano or carboxyl, where $R^4$ is hydrogen; $C_1$–$C_{18}$-alkyl; aryl or hetaryl, which may each be substituted by $C_1$–$C_6$-alkyl, $C_1$–$C_6$-alkoxy, halogen, hydroxyl or cyano;

naphthyl or hetaryl, which may each be substituted by the substituents mentioned for phenyl, in which case the $C_1$–$C_4$-alkyl and $C_1$–$C_6$-alkoxy substituents may be in any desired position on the ring system;

$R^2$ is in each instance independently of the other instances hydrogen; halogen; $C_1$–$C_{18}$-alkyl; aryloxy, arylthio, hetaryloxy or hetarylthio, which may each be substituted by $C_1$–$C_{10}$-alkyl, $C_1$–$C_6$-alkoxy, cyano or carboxyl.

2. Description of the Background

Perylene-3,4-dicarbimides of the formula

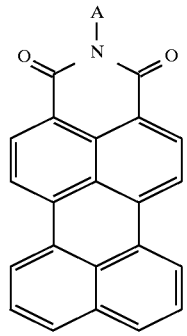

(A: hydrogen or organic radical) are known to be suitable for use as intermediates for making pigment additives, fluorescent dyes and fluorescent pigments (unpublished DE-A-43 25 247; EP-A-596 292; Chimia 48, 503–505 (1994)).

As well as the unsubstituted perylene-3,4-dicarbimide (A=H), only a few N-alkyl- and N-phenyl-substituted perylene-3,4-dicarbimides (A=methyl, ethyl, n-propyl, n-butyl, isobutyl, n-pentyl, n-hexyl, n-octyl, n-dodecyl, phenyl, 4-tolyl, 4-anisyl, 2,5-di-tert-butylphenyl) are known so far and they are prepared by complicated, multistage processes starting from perylene-3,4,9,10-tetracarboxylic dianhydride

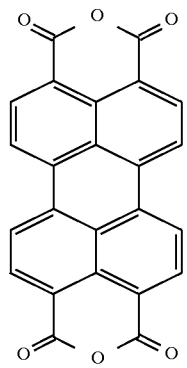

via the corresponding perylene-3,4,9,10-tetracarbimide anhydrides

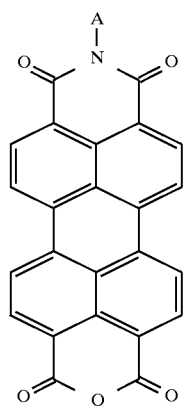

in usually unsatisfactory yields and purities which necessitate costly methods of purification (extraction, column chromatography).

For instance, the unsubstituted and the N-alkyl-substituted perylene-3,4-dicarbimides are obtained by alkaline decarboxylation of the imide-anhydrides at temperatures ≧220° C. under superatmospheric pressure (reaction times of 18 h) (DE-C-486 491; Bulletin of the Chemical Society of Japan 54, 1575–1576 (1981); EP-A 596 292). However, this process is only suitable for aliphatic imides which are stable to bases.

To prepare the N-phenyl-, -tolyl- and -anisyl-substituted (as well as N-methyl- and -ethyl-substituted) perylene-3,4-dicarbimides, the initially prepared unsubstituted perylene-3,4-dicarbimide is sulfonated with sulfuric acid, then converted with potassium hydroxide solution into the sulfonated anhydride, whch is then reacted with the corresponding primary amine to form the sulfonated N-substituted imide, which is finally desulfonated with sulfuric acid to the desired perylene-3,4-dicarbimide (Bulletin of the Chemical Society of Japan 52, 1723–1726 (1979), Shikizai Kyokaishi 49, 29–34 (1976) = Chemical Abstracts 85:209285). This process is very complicated and can only be used for imides which are stable to sulfuric acid.

Finally, it is mentioned in Chimia 48 (1994), 502–505, that N-(2,5-di-tert-butylphenyl)perylene-3,4-dicarbimide can be obtained by condensing perylene-3,4,9,10-tetracarboxylic dianhydride with 2,5-di-tert-butylaniline in the presence of water. However, this reaction likewise yields the imide only in a yield of 50%; moreover, only moderately sterically hindered amines can be reacted in this way.

SUMMARY OF THE INVENTION

It is an object of the present invention to provide a simple and economical process which makes possible the preparation of any desired perylene-3,4-dicarbimides in good yields. It is a further object to develop a simple, inexpensive purifying process to which the imide products can be subjected, if necessary, to increase their purity.

We have found that the first object is achieved by a process for preparing perylene-3,4-dicarbimides by reacting a perylene-3,4,9,10-tetracarboxylic acid or the corresponding anhydrides with a primary amine, which comprises performing the reaction in the presence of a tertiary nitrogen base as solvent and of a transition metal or transition metal salt as catalyst.

We have also found that the second object is achieved by a process for purifying perylene-3,4-dicarbimides obtained by reaction of a perylene-3,4,9,10-tetracarboxylic acid or of the corresponding anhydrides with a primary amine, which comprises first heating the crude products in N-methylpyrrolidone, then treating the resulting N-methylpyrrolidone adducts with a base in the presence of an organic diluent, and, if desired, subjecting the subsequently isolated products to an additional treatment with an aqueous acid.

We have further found a process for making pure perylene-3,4-dicarbimides which comprises combining the process of preparation with this process of purification.

Finally, the present invention provides the perylene-3,4-dicarbimides of the above-defined formula Ia.

Preferred perylene-3,4-dicarbimides Ia are revealed in the subclaims.

DETAILED DESCRIPTION OF THE INVENTION

The process of the invention is suitable for preparing any 9,10-unsubstituted perylene-3,4-dicarbimides. Examples of advantageously obtainable perylene-3,4-dicarbimides have the general formula I

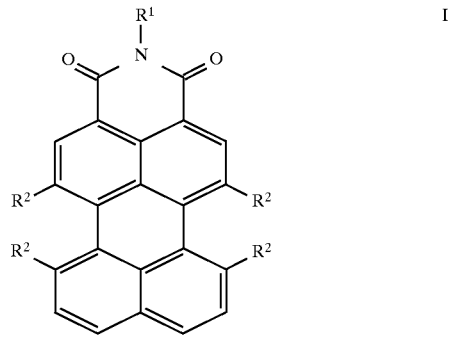

where
$R^1$ is hydrogen;
$C_1$–$C_{30}$-alkyl whose carbon chain may be interrupted by one or more of —O—, —S—, —$NR^3$—, —CO— and/or —$SO_2$— and which may be monosubstituted or polysubstituted by carboxyl, sulfo, hydroxyl, cyano, $C_1$–$C_6$-alkoxy or a 5-, 6- or 7-membered heterocyclic radical which is attached via a nitrogen atom and which may contain further heteroatoms and may be aromatic, where
$R^3$ is hydrogen or $C_1$–$C_6$-alkyl;
$C_5$–$C_8$-cycloalkyl whose carbon skeleton may be interrupted by one or more of —O—, —S— and/or —$NR^3$—;
aryl or hetaryl, which may each be monosubstituted or polysubstituted by $C_1$–$C_{18}$-alkyl, $C_1$–$C_6$-alkoxy, halogen, hydroxyl, cyano, carboxyl, —$CONHR^4$, —$NHCOR^4$ or aryl- and/or hetaryl-azo, which may each be substituted by $C_1$–$C_{10}$-alkyl, $C_1$–$C_6$-alkoxy, halogen, hydroxyl, cyano or carboxyl, where
$R^4$ is hydrogen; $C_1$–$C_{18}$-alkyl; aryl or hetaryl, which may each be substituted by $C_1$–$C_6$-alkyl, $C_1$–$C_6$-alkoxy, halogen, hydroxyl or cyano;
$R^2$ is in each instance independently of the other instances hydrogen; halogen; $C_1$–$C_{18}$-alkyl; aryloxy, arylthio, hetaryloxy or hetarylthio, which may each be substituted by $C_1$–$C_{10}$-alkyl, $C_1$–$C_6$-alkoxy, cyano or carboxyl.

The process of the invention has particular importance for preparing the novel and preferred perylene-3,4-dicarbimides Ia which are defined in the introduction and subclaims.

For instance, amines having a relatively high alkyl chain length (generally >$C_{12}$), which would render the imides insoluble in the aqueous reaction media used in the known processes, amines with modified and/or substituted alkyl chains and also aromatic radicals, which would not be stable under the strongly basic or acid reaction conditions previously used, and especially sterically hindered aromatic amines, in particular o,o'-disubstituted anilines, which can likewise not be used in the known processes, are easy to react with the appropriate perylene-3,4,9,10-tetracarboxylic acids or anhydrides, in particular dianhydrides, which carry the substituents $R^2$.

Any alkyl appearing in the formulae I and Ia may be straight-chain or branched. Substituted aryl may generally include up to 3, preferably 1 or 2, of the substituents mentioned.

Specific examples of suitable radicals $R^1$ and $R^2$ (and of their substituents) are:
methyl, ethyl, propyl, isopropyl, butyl, isobutyl, sec-butyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above designations isooctyl, isononyl, isodecyl and isotridecyl are trivial names derived from the oxo process alcohols—cf. Ullmann's Encyklopädie der technischen Chemie, 4th edition, volume 7, pages 215 to 217, and volume 11, pages 435 and 436);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 4,7-dithiaoctyl, 4,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2-hydroxypropyl, 1-hydroxyprop-2-yl, 2- and 4-hydroxybutyl, 1-hydroxybut-2-yl and 8-hydroxy-4-oxaoctyl, 2-cyanoethyl, 3-cyanopropyl, 2-methyl-3-ethyl-3-cyanopropyl, 7-cyano-7-ethylheptyl and 4-methyl-7-methyl-7-cyanoheptyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

carbamoyl, methylaminocarbonyl, ethylaminocarbonyl, ropylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

formylamino, acetylamino, propionylamino and benzoylamino; chlorine, bromine and iodine;

phenylazo, 2-naphthylazo, 2-pyridylazo and 2-pyrimidylazo;

cyclopentyl, cyclohexyl, cycloheptyl, cyclooctyl, 2-dioxanyl, 4-morpholinyl, 2- and 3-tetrahydrofuryl, 1-, 2- and 3-pyrrolidinyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl)., 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5 and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxyamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl) aminophenyl and 3- and 4-(p-tolyl)aminophenyl; 3- and 4-(2-pyridyl)aminophenyl, 3- and 4-(3-pyridyl) aminophenyl, 3- and 4-(4-pyridyl)aminophenyl, 3- and 4-(2-pyrimidyl)aminophenyl and 4- (4-pyrimidyl) aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The process of the present invention for preparing perylene-3,4-dicarbimides starts from appropriately substituted perylene-3,4,9,10-tetracarboxylic acids and anhydrides, in particular dianhydrides, which can in turn be obtained by halogenation and if desired subsequent replacement of the halogen atoms by aryloxy, arylthio, hetaryloxy, hetarylthio or alkyl radicals.

The particularly interesting, 1,7-disubstituted perylene-3,4,9,10-tetracarboxylic acids and anhydrides are as described in German Patent Applications 195 47 209.8 and 195 47 210.1 obtainable by a multistage process starting from 1,7-dibromoperylene-3,4,9,10-tetracarboxylic acid or dianhydride prepared by selective bromination of perylene-3,4,9,10-tetracarboxylic acid or dianhydride in 100% strength by weight sulfuric acid at from 80° to 90° C. These are reacted in the presence of a polar aprotic solvent such as N-methylpyrrolidone and optionally of an imidation catalyst, for example of an organic or inorganic acid or of a transition metal salt, with a primary amine to form the corresponding 1,7-dibromoperylene-3,4,9,10-tetracarboxylic diimide, which is then reacted either in the presence of an inert aprotic solvent such as N-methylpyrrolidone or of a nonnucleophilic or only weakly nucleophilic base, for example sodium carbonate or potassium carbonate, with an aromatic alcohol or thioalcohol or else in the presence of an aprotic solvent such as tetrahydrofuran, of a palladium complex as catalyst and of a copper salt as cocatalyst and of a base, for example piperidine, with a 1-alkyne. In the last case, 1,7-disubstituted perylene-3,4,9,10-tetracarboxylic diimides are obtained which contain unsaturated bonds in the substituent $R^2$ which are reducible by subsequent stirring in a hydrogen atmosphere or by catalytic reduction with hydrogen. In a last reaction step, the either 1,7-diaroxy-, -diarylthio- or -dialkyl-substituted perylene-3,4,9,10-tetracarboxylic diimide is then saponified in the presence of a polar protic solvent such as isopropanol and of a base, for example sodium hydroxide or potassium hydroxide, to the 1,7-disubstituted perylene-3,4,9,10-tetracarboxylic acid or dianhydride.

In the novel preparation process, the perylene-3,4,9,10-tetracarboxylic acids or their anhydrides, in particular the dianhydrides, are reacted with the desired primary amines (especially $R^1$-$NH_2$) in the presence of a tertiary nitrogen base as solvent and of a transition metal or transition metal salt as catalyst.

This gives rise not only to a unilateral condensation (imidation) reaction but also to a unilateral decarboxylation.

Suitable solvents are in particular those tertiary nitrogen bases whose melting points are below room temperature, since this facilitates reaction mixture workup and solvent recovery.

Examples of suitable bases are cyclic imides such as N-methylpyrrolidone, tertiary aliphatic amines $NR^3$ whose alkyl radicals R have from 4 to 8 carbon atoms, such as trihexylamine, and in particular aromatic heterocycles such as quinaldine, isoquinoline and in particular quinoline.

The amount of solvent is not critical per se; it will usually range from 2 to 20 kg, preferably from 6 to 12 kg, of solvent per kg of perylene-3,4,9,10-tetracarboxylic dianhydride.

Suitable catalysts are in particular the transition metals iron and especially zinc and copper and also in particular their inorganic and organic salts, which are preferably used in anhydrous form.

Examples of preferred salts are copper(I) oxide, copper (II) oxide, copper(I) chloride, copper(II) acetate, zinc acetate and zinc propionate.

It is of course also possible to use mixtures of the catalysts mentioned.

Typically from 5 to 80% by weight of catalyst are used, based on the perylene-3,4,9,10-tetracarboxylic dianhydride. Preferred amounts range from 10 to 25% by weight in the case of the copper compounds and from 40 to 60% by weight in the case of the zinc salts, likewise based on the anhydride.

Suitable primary amines for the preparation process of the invention include all primary amines which are stable at the reaction temperature, preferably those whose boiling point at the reaction pressure is above the reaction temperature.

The reaction temperature is generally from 120° to 250° C., in particular from 170° to 235° C. It is advisable to work under a protective gas atmosphere (eg. nitrogen).

The preparation process of the invention can be carried out at atmospheric pressure or at a superatmospheric pressure of customarily up to 10 bar. The superatmospheric option is advantageous in particular in the case of volatile amines (ie. where the boiling point is $\leq$ about 180° C.).

In general, the molar ratio of the starting compounds amine and anhydride is from 0.8:1 to 6:1. For the atmospheric reaction it is preferably from 0.8:1 to 1.2:1, whereas for the superatmospheric reaction it is in particular from 2:1 to 4:1.

The reaction of the invention is customarily complete within 2–30 h, especially within 3–12 h.

The atmospheric process is advantageously carried out as follows:

Perylene-3,4,9,10-tetracarboxylic dianhydride and catalyst are initially charged in part of the solvent quantity (eg. about half), the apparatus is flushed with nitrogen (about 15 min), the mixture is heated to the reaction temperature under stirring, and a solution of the primary amine in the remaining solvent is added dropwise over about 2–6 h. Following a subsequent stirring time of customarily about 0.5–8 h at the reaction temperature, the batch is cooled down to 120°–140° C., and unconverted anhydride and the bulk of the catalyst are filtered off at that temperature.

The rest of the workup of the filtrate, cooled down to room temperature, for the (crude) products (perylene-3,4-dicarbimide contaminated by varying amounts of diimide) can be carried out in a conventional manner by, if necessary after addition of primary alcohols such as methanol to complete the precipitation, filtering off the precipitated products and washing and drying them.

In the case of the preparation of perylene-3,4-dicarbimides which are no longer soluble in the solvent at temperatures $\leq$ about 140° C. (eg. N-(4-phenylazophenyl) perylene-3,4-dicarbimide), these imides are advantageously filtered off at that temperature, the filter cake is washed preferably with hot (likewise about 130° C.) solvent and methanol, and the washed filter cake is boiled for from 0.5 to 1 h in dilute inorganic acid (for example 10–15% strength by weight hydrochloric acid) for complete removal of the catalyst. Subsequently the imides can be isolated in a conventional manner by filtration of the cooled mixture, washing with water until the wash liquor runoff is neutral and salt-free, and drying.

Generally, the products thus treated are already sufficiently pure (>95%) as to require no further purification.

The superatmospheric process is advantageously carried out by initially charging perylene-3,4,9,10-tetracarboxylic dianhydride, catalyst and primary amine in all of the solvent, flushing the pressure apparatus with nitrogen (about 15 min), closing the pressure apparatus, setting a nitrogen pressure of generally 1–2 bar, and then heating the stirred mixture to the reaction temperature and maintaining it at that temperature for about 6–8 h. After cooling down to customarily 120°–140° C. and decompressing, the reaction mixture can be worked up as described above.

If the (crude) products obtained in the preparation process of the invention do not meet the desired purity requirements (the products obtained generally have purities $\geq$80%), they can additionally be subjected to the purification process of the invention.

In the purification process of the invention, the crude perylene-3,4-dicarbimide products are initially heated in N-methylpyrrolidone (NMP) to convert them into NMP adducts. If the imide was prepared using NMP as solvent, this step can of course be omitted.

The NMP adducts are subsequently subjected to an alkaline purification treatment. If desired, it can be followed by an acid aftertreatment.

The first step of the purification process of the invention, the formation of the NMP adducts, is customarily carried out by heating the dried crude product in about 3–10 times, preferably 5.5–6.5 times, the weight of NMP, with stirring to about 140°–200° C., preferably 160°–180° C., particularly preferably 165°–170° C., generally maintaining this temperature for 10–60 min, in particular 15–30 min. This treatment is advantageously carried out under protective gas (eg. nitrogen).

Advantageously the mixture is then cooled down, preferably with slow stirring, initially to about 50°–55° C. and then without stirring to room temperature.

The NMP adduct can then be isolated in a conventional manner by filtration, washing (preferably first with a mixture of NMP and water-soluble alcohol such as ethanol, then with dilute hydrochloric acid, and finally with water) with or without drying.

The second step of the purification process of the invention, the alkaline treatment of the NMP adduct, is advantageously carried out in the precence of an organic reaction medium.

Suitable organic diluents include not only inert aromatic solvents such as toluene and xylene but also, with preference, alcohols which can be monohydric or polyhydric, for example aromatic alcohols such as phenol and benzyl alcohol and aliphatic alcohols, not only glycols and glycol ethers, such as ethylene glycol, propylene glycol and butylglycol (ethylene glycol monobutyl ether) but also, in particular, $C_2-C_6$-alcohols such as ethanol, propanol, butanol, pentanol and hexanol, which each may also be branched, such as, preferably, isopropanol.

In general, the diluent is used in an amount of from 40 to 200 kg, in particular from 80 to 120 kg, per kg of NMP adduct.

Suitable bases include not only sterically hindered nitrogen bases, such as diazabicycloundecene and diazabicyclo [2.2.2]octane, but especially alkali metal hydroxides, such as sodium hydroxide and in particular potassium hydroxide, and alkali metal salts of secondary and tertiary aliphatic (preferably $C_3-C_6$) alcohols, such as sodium tert-butoxide and in particular potassium tert-butoxide.

The alkali metal hydroxides are advantageously used together with water (for example from 40 to 60% by weight, based on the alkali metal hydroxide).

It is customary to use from 2 to 15 kg of base per kg of NMP adduct, preferably from 5 to 7 kg, in particular about 6 kg, of dry alkali metal hydroxide or from 0.5 to 1.5 kg, in particular from 0.7 to 1 kg, of alkoxide or nitrogen base.

It is advisable to carry out the alkaline treatment at elevated temperature. The treatment temperature is generally from 50° to 150° C., preferably from 60° to 120° C.

An advantageous procedure is to charge the diluent initially, add the NMP adduct and the base, and then heat the mixture with stirring to the treatment temperature, maintaining said temperature for about 1–24 h, in particlar 1–10 h.

The purified product can be isolated in a conventional manner by cooling to about 25°–30° C., if necessary completing the precipitation by adding methanol, filtering off the precipitate, washing the filter cake (preferably with the diluent used for the purification, methanol and water) and drying.

If desired, it is possible to follow this up with an additional acid treatment by suspending the undried filter cake in a dilute inorganic acid, for example 4–6% strength by weight hydrochloric acid (about 4–6 kg of acid per kg of filter cake).

The purified imide can then be isolated in a conventional manner by filtration, washing with water (until the wash liquor running off is neutral) and drying.

The additional acid treatment is advisable in particular in the case of perylene-3,4-dicarbimides of the formula I where $R^1$ is phenyl or $C_1-C_4$-alkyl-substituted phenyl and $R^2$ is hydrogen.

The novel process for making pure perylene-3,4-dicarbimides constitutes an advantageous combination of the preparation process of the invention with the purifying process of the invention. It yields any desired perylene-3,4-dicarbimides in a technically simple and economical manner in excellent purities (generally >98%) and good yields (generally 60–90%).

The novel perylene-3,4-dicarbimides Ia, as well as the imides I prepared according to the invention, are advantageously useful not only as pigment additive precursors but also as pigments or fluorescent dyes. They can be used in particular for coloring macromolecular organic materials or else organic/inorganic composites.

Suitable pigments are in particular the perylene-3,4-dicarbimides Ia where $R^{1'}$ is phenyl or monocyclic hetaryl (in particular pyridyl or pyrimidyl), which is each monosubstituted, disubstituted or trisubstituted by $C_1-C_4$-alkyl and/or cyano or monosubstituted by phenylazo or naphthylazo, and $R^2$ is hydrogen.

Suitable fluorescent dyes are in particular the perylene-3,4-dicarbimides Ia where $R^{1'}$ is phenyl or monocyclic hetaryl (in particular pyridyl or pyrimidyl), which is in each case monsubstituted, disubstituted or trisubstituted by hydroxyl, carboxyl, —$CONHR^4$ and/or —$NHCOR^4$ ($R^4$: $C_1-C_4$-alkyl or phenyl which may be substituted by $C_1-C_4$-alkyl or $C_1-C_4$-alkoxy), or $C_5-C_8$-cycloalkyl, and $R^2$ is hydrogen or phenoxy which may be monosubstituted, disubstituted or trisubstituted by $C_1-C_4$-alkyl.

EXAMPLES

A) Preparation of perylene-3,4-dicarbimides of the formula Ib

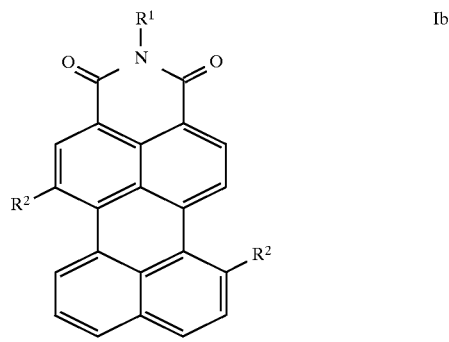

from the corresponding perylene-3,4,9,10-tetracarboxylic dianhydrides of the formula II

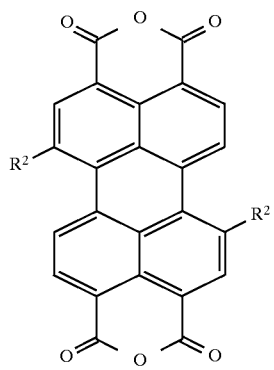

The 1,7-disubstituted perylene-3,4,9,10-tetracarboxylic dianhydrides II used as starting material for the 1,7-disubstituted perylene-3,4-dicarbimides (Examples 25 to 27) were prepared as follows.

a) Preparation of 1,7-dbromoperylene-3,4,9,10-tetracarboxylic dianhydride (IIa)

Example 1

A mixture of 292.5 g (0.75 mol) of perylene-3,4,9,10-tetracarboxylic dianhydride (purity >98%) and 4420 g of 100% strength by weight sulfuric acid was heated to 85° C. following stirring for 12 hours and subsequent addition of 7 g of iodine. 262.5 g (1.64 mol) of bromine were then added dropwise over 8 h.

After cooling down to room temperature and displacing the excess bromine by nitrogen, the sulfuric acid concentration of the reaction mixture was reduced to 86% by weight by adding a total of 670 g of water a little at a time over 1 h. After cooling the reaction mixture, which had heated up to 85° C. in the course of the addition, to room temperature, the precipitated product was filtered off on a G4 glass frit, washed with 3 kg of 86% strength by weight sulfuric acid, then suspended in 5 l of water, filtered off again, washed neutral and dried under reduced pressure at 120° C.

This gave 370 g of IIa in the form of a luminously red, finely crystalline powder having a melting point >360° C. and a purity >98%, which corresponds to a yield of 90%.

b) Preparation of N,N'-dicyclohexyl-1,7-dibromoperylene-3,4,9,10-tetracarboxylic diimide (III)

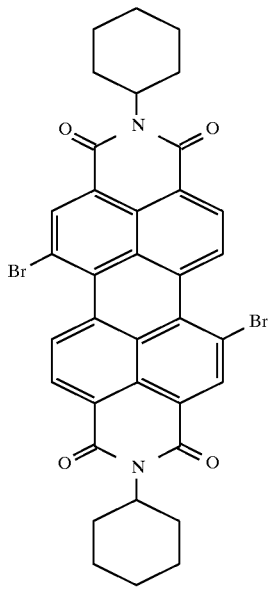

Example 2

To a mixture of 69.9 g (127 mmol) of 1,7-dibromoperylene-3,4,9,10-tetracarboxylic dianhydride (IIa) (Example 1) in 900 ml of N-methyl-2-pyrrolidone were initially added with stirring 42.8 g of glacial acetic acid and then, a little at a time, a total of 381 mmol of cyclohexylamine. The reaction mixture was then heated under nitrogen to 85° C. and stirred at that temperature for 6 h.

After cooling down to room temperature, the precipitated reaction product was filtered off, washed with a total of 2 l of methanol and dried under reduced pressure at 100° C.

This gave 75.1 g of IVa as a bright red, microcrystalline powder having a melting point >360° C. and a purity of 97%, which corresponds to a yield of 83%.

Analytical data: Elemental analysis (% by weight calc./obs.): C: 60.7/60.3; H: 4.0/4.2; N: 3.9/3.8; O: 9.0/9.3; Br: 22.4/22.0; IR (KBr): ν=1698 (s, C=O), 1655 (s, C=O) cm$^{-1}$; UV/VIS (CHCl$_3$): λ$_{max}$ (ε)=491 (33411), 526 (50033) nm.

c) Preparation of 1,7-diaroxy-substituted N,N'-dicyclohexylperylene-3,4,9,10-tetracarboxylic diimides IV

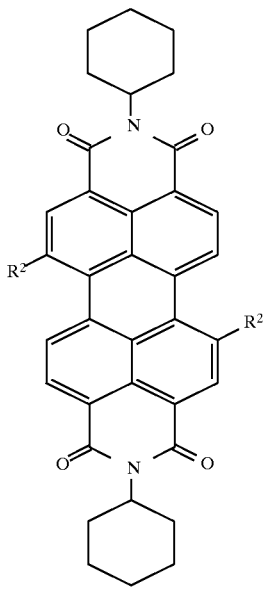

IV

Examples 3 and 4

14.25 g (20 mmol) of N,N'-dicyclohexyl-1,7-dibromoperylene-3,4,9,10-tetracarboxylic diimide (III) from Example 2 were added with stirring to 450 ml of N-methylpyrrolidone, successively admixed with 6.4 g (46 mmol) of anhydrous potassium carbonate and a g (40 mmol) of the hydroxyaromatic $R^2$-H, and heated under nitrogen at 120° C. for 1.5 h.

After cooling down to room temperature, the reaction mixture was added with stirring to 1.5 l of 6% strength by weight hydrochloric acid. The precipitated reaction product was filtered off, washed neutral with water and dried under reduced pressure at 100° C.

Further details concerning these experiments and their results are collated in Table 1.

($M^+$, 100%); IR (KBr): $\nu$=1695 (s, C=O), 1654 (s, C=O) $cm^{-1}$; UV/VIS ($CHCl_3$): $\lambda_{max}$ ($\epsilon$)=401 (7455), 513 (37102), 549 (55004) nm.

Analytical data to Example 4:

Elemental analysis (% by weight calc./obs.): C: 79.0/78.8; H: 6.4/6.4; N: 3.3/3.2; O: 11.3/11.4; Mass (FD): m/z=850 ($M^+$, 100%); IR (KBr): $\nu$=1697 (s, C=O), 1654 (s, C=O) $cm^{-1}$; UV/VIS ($CHCl_3$): $\lambda_{max}$ ($\epsilon$)=404 (9447), 512 (34785), 547 (52117) nm.

d) Preparation of 1,7-diaroxy-substituted perylene-3,4,9,10-tetracarboxylic dianhydrides II

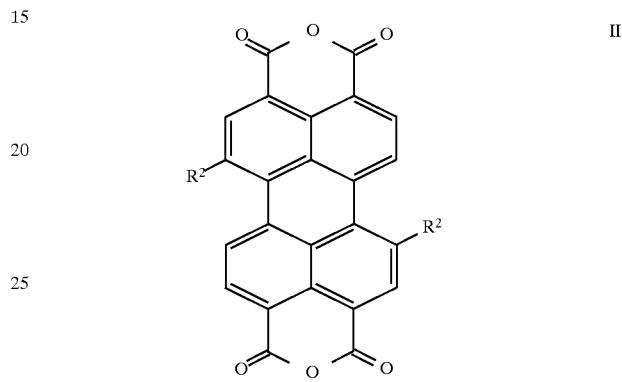

II

Examples 5 and 6

A mixture of, in each case, 10 g of the N,N'-dicyclohexyl-1,7-diaroxyperylene-3,4,9,10-tetracarboxylic diimide (IV) of Example 3 or 4, 1 l of isopropanol, 65 g of potassium hydroxide and 26 g of water was refluxed for 5 h.

After cooling down to room temperature, the precipitated reaction product was filtered off, washed with isopropanol to a colorless run-off, then added with stirring to 1 l of 10% strength by weight hydrochloric acid and briefly heated to the boil. After cooling down to room temperature, the product was again filtered off, washed neutral with water and dried under reduced pressure at 100° C.

TABLE 1

| | | Result | | | |
|---|---|---|---|---|---|
| Ex. $R^2$ | Hydroxy-a g aromatic $R^2$-H | Yield [g]/[%] | Purity [%] | Appearance | m.p. [°C.] |
| 3 Phenoxy | 3.8 Phenol | 14.5/98 | 93 | dark red, crystalline | >360 |
| 4 p-tert-Butylphenoxy | 6.0 p-tert-Butyl-phenol | 16.0/94 | 95 | magenta, micro-crystalline | >360 |

Analytical data to Example 3:

Elemental analysis (% by weight calc./obs.): C: 78.0/77.5; H: 5.2/5.3; N: 3.8/3.7; O: 13.0/13.4; Mass (FD): m/z=738

Further details of these experiments and their results are collated in Table 2. The purity of the products was determined by UV/VIS spectroscopy and semiquantitative thin layer chromatography over silica gel using trichloroacetic acid/toluene as mobile phase.

TABLE 2

| Ex. | R² | Diimide IV of Ex. | Yield [g]/[%] | Purity [%] | Appearance | m.p. [°C.] |
|---|---|---|---|---|---|---|
| 5 | Phenoxy | 3 | 7.4/94 | 98 | reddish violet, microcrystalline | >360 |
| 6 | p-tert-Butylphenoxy | 4 | 7.7/95 | 98 | reddish violet, amorphous | >360 |

Analytical data to Example 5:

Elemental analysis (% by weight calc./obs.) C: 75.0/74.8; H: 2.8/2.8; O: 22.2/22.3; IR (KBr): ν=1758 (s, C=O), 1729 (s, C=O) cm$^{-1}$; UV/VIS (H$_2$SO$_4$): $\lambda_{max}$ (ε)=415 (8832), 559 (38103) nm.

Analytical data to Example 6: Elemental analysis (% by weight calc./obs.) C: 76.7/76.6; H: 4.7/4.7; O: 18.6/18.7; IR (KBr): ν=1755 (s, C=O), 1730 (s, C=O); UV/VIS (H$_2$SO$_4$): $\lambda_{max}$ (ε)=412 (9405), 561 (32746) nm.

Examples 7 to 27

1) Preparation Under Atmospheric Pressure (Method M1)

A suspension of 50 mmol of perylene-3,4,9,10-tetracarboxylic dianhydride II and x g of catalyst K in 100 ml of quinoline was heated with stirring to T°C. under nitrogen. Then a solution of 50 mmol (Example 22: 55 mmol; Example 23: 52 mmol) of the primary amine R$^1$NH$_2$ in 80–100 ml of quinoline was added dropwise over 3–3.5 h (Examples 7, 8 and 24: 6 h).

Following a subsequent stirring time of t h at T°C., the batch was cooled down to about 130° C. and filtered through a preheated G4 glass frit. After cooling the filtrate down to room temperature, the precipitated crude product was filtered off, washed with methanol and dried under reduced pressure. Methanol was carefully added to the filtrate to complete the precipitation, and the precipitated, more contaminated crude product was isolated as described above and combined with the bulk quantity.

In Example 23, the crude product, which actually came down as a precipitate at 130°–140° C., was filtered off, washed initially with a little hot quinoline at 130° C. and then with methanol, and subsequently heated in 500 ml of 10% strength by weight hydrochloric acid at 80° C. for 0.5 h with stirring. The hot suspension was filtered, and the filter cake was washed neutral and salt-free with water and likewise dried under reduced pressure.

2) Preparation Under Superatmospheric Pressure (Method M2)

In a 1 l stirred autoclave, a mixture of 0.2 mol (78.4 g) of perylene-3,4,9,10-tetracarboxylic dianhydride, x g of catalyst K, 0.6 mol of the primary amine R$^1$NH$_2$, and 400 ml of quinoline was flushed with nitrogen for 15 min. After the autoclave had been sealed pressure-tight, a pressure of 2 bar of nitrogen was preset and the autoclave was then heated to T°C.

Following a subsequent stirring time of t h at T°C. and a superatmospheric pressure of more than 3 bar, the contents were cooled down to about 130° C., decompressed and worked up as described in general terms in connection with method M1.

Further details of these experiments and their results are summarized in Table 3.

TABLE 3

| Ex. | R¹ | R² | x g | K | M | T°C. | t h | Crude yield in % (based on II) | Purity in % |
|---|---|---|---|---|---|---|---|---|---|
| 7 | 2,6-Diisopropylphenyl | H | 3.6 | Copper(I) oxide | M1 | 230 | 2.5 | 79 | 90 |
| 8 | 2,6-Diisopropylphenyl | H | 9.8 | Zinc propionate | M1 | 230 | 4.5 | 75 | 85 |
| 9 | 2,6-Diisopropylphenyl | H | 9.8 | Zinc acetate | M1 | 230 | 4.0 | 72 | 85 |
| 10 | 2,6-Diisopropylphenyl | H | 12.0 | Copper(I) oxide | M2 | 200 | 9.0 | 70 | 80 |
| 11 | Phenyl | H | 16.2 | Zinc propionate | M1 | 230 | 11.0 | 94 | 80 |
| 12 | Phenyl | H | 16.2 | Zinc acetate | M1 | 230 | 7.0 | 92 | 85 |
| 13 | Phenyl | H | 2.9 | Copper(I) oxide | M1 | 200 | 1.0 | 84 | 85 |
| 14 | 2-Methylphenyl | H | 2.0 | Copper(I) oxide | M1 | 200 | 1.5 | 78 | 85 |
| 15 | 2,4,6-Trimethylphenyl | H | 16.2 | Zinc propionate | M1 | 230 | 5.5 | 89 | 80 |
| 16 | 2-Pyridyl | H | 2.0 | Copper(I) oxide | M1 | 200 | 1.0 | 73 | 80 |
| 17 | 2-Pyrimidyl | H | 16.2 | Zinc propionate | M1 | 230 | 3.0 | 79 | 90 |
| 18 | 4-Acetylaminophenyl | H | 2.9 | Copper(I) oxide | M1 | 200 | 2.0 | 91 | 90 |
| 19 | 5-Nonyl | H | 2.0 | Copper(I) oxide | M1 | 200 | 1.5 | 86 | 75 |
| 20 | Dodecyl | H | 16.2 | Zinc acetate | M1 | 230 | 6.0 | 60 | 90 |
| 21 | Dodecyl | H | 2.0 | Copper(I) oxide | M1 | 180 | 1.0 | 70 | 80 |
| 22 | Octadecyl | H | 16.2 | Zinc acetate | M1 | 230 | 5.5 | 57 | 90 |
| 23 | 4-Phenylazophenyl | H | 2.0 | Copper(I) oxide | M1 | 180 | 1.5 | 79 | >99 |
| 24 | 3,5-Dimethylphenyl | H | 3.2 | Copper(I) oxide | M1 | 200 | 2.0 | 89 | 85 |
| 25 | 2,6-Diisopropylphenyl | Br | 3.0 | Copper(I) oxide | M1 | 200 | 1.0 | 82 | 90 |
| 26 | 3,5-Dimethylphenyl | Phenoxy | 3.0 | Copper(I) oxide | M1 | 160 | 1.0 | 79 | 90 |

TABLE 3-continued

| Ex. | R¹ | R² | x g | K | M | T°C. | t h | Crude yield in % (based on II) | Purity in % |
|---|---|---|---|---|---|---|---|---|---|
| 27 | 3,5-Dimethylphenyl | p-tert-Butyl-phenoxy | 3.0 | Copper(I) oxide | M1 | 160 | 1.0 | 77 | 90 |

These are analytical data for the imides of Examples 23, 24 and 26.

Example 23

N-(4-Phenylazophenyl)perylene-3,4-dicarbimide red powder of m.p. >360° C.;

Elemental analysis (% by weight calc./obs.): C: 81.4/80.8; H: 3.8/3.7; N: 8.4/8.3; O: 6.4/6.9; Mass (EI): m/z=501 (M⁺), 396 (M⁺-PhN₂; 100%); IR (KBr): ν=1688 (s, C=O), 1650 (s, C=O) cm⁻¹; UV/VIS (H₂SO₄): $\lambda_{max}$ (ε)=413 (27691), 577 (27227), 614 (140738) nm.

Example 24

N-(3,5-Dimethylphenyl)perylene-3,4-dicarbimide reddish orange crystals of m.p. >360° C.;

Elemental analysis (% by weight calc./obs.): C: 84.7/84.5; H: 4.5/4.5; N: 3.3/3.3; O: 7.5/7.6; Mass (EI): m/z=425 (M⁺; 100%); IR (KBr): ν=1695 (s, C=O), 1653 (s, C=O) cm⁻¹; UV/VIS (CHCl₃): $\lambda_{max}$ (ε)=265 (29378), 487 (30930), 510 (29375) nm; ¹H-NMR (300 MHz, CDCl₃): δ=8.57 (d, 2H); 8.47 (t, 4H); 7.94 (d, 2H); 7.71–7.64 (dd, 2H); 7.15 (s, with nuclear coupling, 1H); 6.94 (s, 2H) ppm.

Example 26

N-(3,5-Dimethylphenyl)-1,7-diphenoxyperylene-3,4-dicarbimide blackish violet crystals of m.p. 125°–127° C.;

Elemental analysis (% by weight calc./obs.): C: 82.7/82.5; H: 4.5/4.5; N: 2.3/2.3; O: 10.5/10.6; Mass (EI): m/z=609 (M⁺; 100%), 517 (M⁺-OPh; 58%); IR (KBr): ν=1703 (s, C=O), 1670 (s, C=O) cm⁻¹; UV/VIS (NMP): $\lambda_{max}$ (ε)= 361 (7863), 516 (52443), 742 (722) nm.

B) Purification of perylene-3,4-dicarbimides of the formula Ib

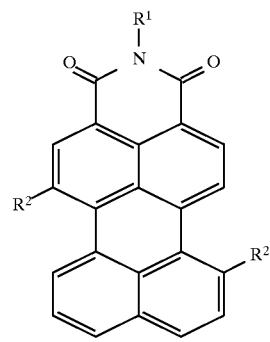

Ib

Examples 28 to 33

A mixture of x g of the crude product of Example 7 (12; 14; 16; 22; 25) and 100 g of N-methylpyrrolidone (NMP) was heated at 165° C. for 15 min with stirring, then cooled down to 50°–55° C. with slow stirring and finally down to room temperature without stirring. The precipitated NMP adduct was filtered off, successively washed with 28 g of NMP, 22 g of ethanol and 68 g of 6% strength by weight hydrochloric acid, then suspended in water, again filtered off, washed neutral with water and dried under reduced pressure.

The dried NMP adduct was comminuted and heated in a mixture of 1500 ml of isopropanol, 90.5 g of potassium hydroxide (85% strength) and 35 ml of water under reflux (about 82° C.) for t h. After cooling at 25° C., the precipitate was filtered off, washed successively with isopropanol, a little methanol and water, subsequently suspended in 100 ml of 5% strength by weight hydrochloric acid, again filtered off, washed neutral with water and dried under reduced pressure.

Further details of these experiments and their results are listed in Table 4.

TABLE 4

| Ex. | R¹ | R² | x g | Crude product of Ex. | t h | Yield in % [based on crude product] | Purity in % | Appearance | m.p. °C. |
|---|---|---|---|---|---|---|---|---|---|
| 28 | 2,6-Diiso-propylphenyl | H | 15.7 | 7 | 10.0 | 89 | >99 | luminous red, crystalline | >300 |
| 29 | Phenyl | H | 15.0 | 12 | 5.5 | 79 | >98 | brownish red, amorphous | >360 |
| 30 | 2-Methyl-phenyl | H | 15.0 | 14 | 6.0 | 83 | >99 | dark red, crystalline | >360 |
| 31 | 2-Pyridyl | H | 15.0 | 16 | 10.0 | 71 | >98 | brownish red, amorphous | >360 |
| 32 | Octadecyl | H | 15.0 | 22 | 4.0 | 87 | >99 | reddish orange, amorphous | 175–176 |

TABLE 4-continued

| Ex. | R$^1$ | R$^2$ | x g | Crude product of Ex. | t h | Yield in % [based on crude product] | Purity in % | Appearance | m.p. °C. |
|---|---|---|---|---|---|---|---|---|---|
| 33 | 2,6-Diiso-propylphenyl | Br | 15.0 | 25 | 7.0 | 85 | >98 | reddish violet, amorphous | >300 |

These are analytical data for the purified imides.

Example 28

N-(2,6-Diisopropylphenyl)perylene-3,4-dicarbimide $^1$H-NMR (300 MHz, CDCl$_3$): δ=8.60 (d, 2H); 8.37 (d, 2H); 8.35 (d, 2H); 7.85 (d, 2H); 7.58 (t, 2H); 7.4–7.5 (dd, 1H); 7.33 (d, 2H); 2.77 (m, 2H); 1.18 (d, 12H) ppm; $^{13}$C-NMR (75.5 MHz, CDCl$_3$): δ=164.0; 145.7; 137.5; 134.3; 131.9; 131.1; 130.9; 130.5; 129.4; 129.2; 127.9; 127.0; 124.0; 123.8; 121.0; 120.1; 29.1; 24.0 ppm; IR (KBr): ν=1696 (s, C=O), 1656 (s, C=O) cm$^{-1}$; UV/VIS (CH$_2$Cl$_2$): λ$_{max}$ (ε)=263 (33565), 484 (33241), 506 (32061) nm.

Example 29

N-Phenylperylene-3,4-dicarbimide

Mass (EI): m/z=397 (M$^+$; 100%) IR (KBr): ν=1698 (s, C=O), 1651 (s, C=O) cm$^{-1}$; UV/VIS (NMP): λ$_{max}$ (ε)= 354 (2890), 498 (29638) nm.

Example 30

N-(2-Methylphenyl)perylene-3,4-dicarbimide

Mass (EI): m/z=411 (M$^+$), 394 (M$^+$+H-H$_2$O; 100%); IR (KBr): ν=1682 (s, C=O), 1652 (s, C=O) cm$^{-1}$; UV/VIS (NMP): λ$_{max}$ (ε)=355 (3223), 503 (32014) nm.

Example 31

N-(2-Pyridyl)perylene-3,4-dicarbimide

Mass (FD): m/z=398 (M$^+$; 100%); IR (KBr): ν=1700 (s, C=O), 1654 (s, C=O) cm$^{-1}$; UV/VIS (NMP): λ$_{max}$ (ε)= 352 (2541), 501 (30328) nm.

Example 32

N-Octadecylperylene-3,4-dicarbimide $^1$H-NMR (250 MHz, CD$_2$Cl$_2$): δ=8.37 (d, 2H); 8.25 (d, 2H); 8.19 (d, 2H); 7.77 (d, 2H); 7.50 (t, 2H); 4.05 (t, 2H); 1.15–142 (m, 32H); 0.81 (t, 3H) ppm; Mass (FAB): m/z=573 (M$^+$), 321 (M$^+$-C$_{18}$H$_{25}$; 100%); IR (KBr): ν=1680 (m, C=O), 1649 (s, C=O) cm$^{-1}$; UV/VIS (H$_2$SO$_4$): λ$_{max}$ (ε)=410 (6158), 574 (21297), 613 (168942) nm.

Example 33

N-(2,6-Diisopropylphenyl)-1,7-dibromoperylene-3,4-dicarbimide

Mass (EI): m/z=642/640/638(M$^+$, $^{79}$Br/$^{81}$Br), 560/558 (M$^+$-Br; 100%); IR (KBr): ν=1695 (s, C=O), 1656 (s, C=O) cm$^{-1}$; UV/VIS (H$_2$SO$_4$): λ$_{max}$ (ε)=399 (13521), 548 (41551) nm.

We claim:

1. A process for preparing perylene-3,4-dicarbimides by reacting a perylene-3,4,9,10-tetracarboxylic acid or the corresponding anhydrides with a primary amine, which comprises performing the reaction in a reaction medium consisting essentially of a tertiary nitrogen base as solvent and of a transition metal or transition metal salt as catalyst.

2. A process as claimed in claim 1, wherein the tertiary nitrogen base used is a nitrogen-containing heteroaromatic.

3. A process as claimed in claim 1, wherein the catalyst used is zinc, a zinc salt, copper, a copper salt or a mixture thereof.

4. A process for purifying perylene-3,4-dicarbimides obtained by reaction of a perylene-3,4,9,10-tetracarboxylic acid or of the corresponding anhydrides with a primary amine, which comprises first heating the crude products in N-methylpyrrolidone, then treating the resulting N-methylpyrrolidone adducts with a base in the presence of an organic diluent, and, if desired, subjecting the subsequently isolated products to an additional treatment with an aqueous acid.

5. A process as claimed in claim 4, wherein the base used is an alkali metal hydroxide or an alkali metal alkoxide.

6. A process for making pure perylene-3,4-dicarbimides by reacting a perylene-3,4,9,10-tetracarboxylic acid or the corresponding anhydrides with a primary amine, which comprises performing the reaction in the presence of a tertiary nitrogen base as solvent and of a transition metal or transition metal salt as catalyst and first heating the resulting crude products in N-methylpyrrolidone, then treating the resulting N-methylpyrrolidone adducts with a base in the presence of an organic diluent, and, if desired, subjecting the subsequently isolated products to an additional treatment with an aqueous acid.

7. Perylene-3,4-dicarbimides of the general formula Ia

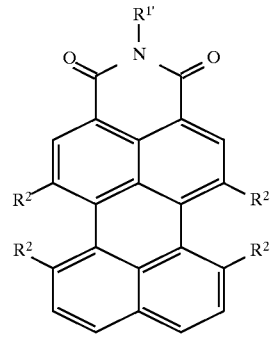

Ia where

R$^{1'}$ is C$_{14}$–C$_{30}$-alkyl whose carbon chain may be interrupted by one or more of —O—, —S—, —NR$^3$—, —CO— and/or —SO$_2$— and which is monosubstituted or polysubstituted by carboxyl, sulfo, hydroxyl, cyano, C$_1$–C$_6$-alkoxy or a 5-, 6- or 7-membered heterocyclic radical which is attached via a nitrogen atom and which may contain further heteroatoms and may be aromatic, where R$^3$ is hydrogen or C$_1$–C$_6$-alkyl; or R$^{1'}$ is C$_5$–C$_8$- cycloalkyl whose carbon skeleton is interrupted by one or more of —O—, —S—, and/or —NR$^3$—; or R$^{1'}$ is phenyl which is polysubstituted by C$_1$–C$_4$-alkyl or methoxy at least in the two ortho positions, and/or monosubstituted or polysubstituted by C$_5$–C$_{18}$-alkyl, C$_2$–C$_6$-alkoxy, halogen, hydroxyl, cyano, carboxyl, —CONHR$^4$, —NHCOR$^4$ and/or aryl- or hetaryl-azo, which may each be substituted by C$_1$–C$_{10}$-alkyl, C$_1$–C$_6$-alkoxy, halogen, hydroxyl, cyano or carboxyl, where R$^3$ is as above defined, and R$^4$ is hydrogen, C$_1$–C$_{18}$-alkyl, aryl or hetaryl, wherein the aryl or hetaryl may each be substituted by C$_1$–C$_6$-alkyl, C$_1$–C$_6$-alkoxy, halogen, hydroxyl or cyano, or R$^{1'}$ is naphthyl or hetaryl, which may each be substituted by a radical defined as substituents for phenyl, in which case the C$_1$–C$_4$-alkyl and C$_1$–C$_6$-alkoxy substituents may be in any desired position on the ring system;

R$^2$ is in each instance independently of the other instances hydrogen; halogen; C$_1$–C$_{18}$-alkyl; aryloxy, arylthio, hetaryloxy or hetarylthio, which may each be substituted by C$_1$–C$_{10}$-alkyl, C$_1$–C$_6$-alkoxy, cyano or carboxyl.

8. Perylene-3,4-dicarbimides as claimed in claim 7 of the formula Ia where R$^{1'}$ is C$_{14}$–C$_{30}$-alkyl which is monosubstituted by carboxyl, sulfo, hydroxyl or a 5-, 6- or 7-membered heterocyclic radical which is attached via a nitrogen atom and which may contain further heteroatoms and may be aromatic; phenyl which is polysubstituted by C$_1$–C$_4$-alkyl at least in the two ortho positions, or monosubstituted or polysubstituted by halogen, hydroxyl, cyano, carboxyl, —COHNR$^4$ or —NHCOR$^4$ and/or monosubstituted by aryl- or hetaryl-azo, which may each be substituted by C$_1$–C$_{10}$-alkyl, C$_1$–C$_6$-alkoxy, halogen, hydroxyl, cyano or carboxyl; hetaryl which may be substituted by the radicals defined as above substituents for phenyl and/or by C$_1$–C$_4$-alkoxy, in which case the C$_1$–C$_4$-alkyl substituents may be in any desired position on the ring system;

R$^2$ is in each instance independently of the other instances hydrogen, halogen or phenoxy which may be substituted by C$_1$–C$_6$-alkyl, C$_1$–C$_6$-alkoxy, cyano or carboxyl.

9. Perylene-3,4-dicarbimides as claimed in claim 7 of the formula Ia where R$^{1'}$ is C$_{14}$–C$_{30}$-alkyl which is monosubstituted by carboxyl, sulfo or hydroxyl; phenyl which is substituted by C$_1$–C$_4$-alkyl in both ortho positions, hydroxyl, cyano, carboxyl, —CONHR$^4$ or —NHCOR$^4$, where R$^4$ is C$_1$–C$_4$-alkyl or phenyl which may be substituted by C$_1$–C$_4$-alkyl, C$_1$–C$_4$-alkoxy or cyano, or by phenyl- or naphthyl-azo which may be substituted by C$_1$–C$_4$-alkyl, C$_1$–C$_4$-alkoxy, hydroxyl or cyano; monocyclic hetaryl which may be monosubstituted or polysubstituted by C$_1$–C$_4$-alkyl, C$_1$–C$_4$-alkoxy, hydroxyl or cyano or monosubstituted by phenyl- or naphthyl-azo which may be substituted by C$_1$–C$_4$-alkyl, C$_1$–C$_4$-alkoxy, hydroxyl or cyano;

R$^2$ is in each instance independently of the other instances hydrogen or phenoxy which may be substituted by C$_1$–C$_4$-alkyl.

10. A method of coloring comprising contacting the perylene-3,4-dicarbimides of the formula Ia as set forth in claim 7 with an organic or organic/inorganic composite material.

* * * * *